(12) United States Patent
Danda et al.

(10) Patent No.: US 7,528,280 B2
(45) Date of Patent: May 5, 2009

(54) PROCESS FOR THE PREPARATION OF BIPHOSPHONIC ACIDS

(75) Inventors: Subba Reddy Danda, Hyderabad (IN); Narayan K. A. S. S. Garimella, Hyderabad (IN); Srinivasa Rao V. N Divvela, Hyderabad (IN); Ramesh Dandala, Hyderabad (IN); Sivakumaran Meenakshisunderam, Hyderabad (IN)

(73) Assignee: Aurobindo Pharma Ltd., Hyderabad (IN)

( * ) Notice: Subject to any disclaimer, the term of this patent is extended or adjusted under 35 U.S.C. 154(b) by 0 days.

(21) Appl. No.: 11/655,027

(22) Filed: Jan. 18, 2007

(65) Prior Publication Data

US 2007/0173645 A1 Jul. 26, 2007

(30) Foreign Application Priority Data

Jan. 20, 2006 (IN) .......................... 95/CHE/2006

(51) Int. Cl.
*C07F 9/38* (2006.01)
(52) U.S. Cl. ................ 562/13; 562/8; 562/11
(58) Field of Classification Search ................ 562/13, 562/8, 11
See application file for complete search history.

(56) References Cited

U.S. PATENT DOCUMENTS

| | | | |
|---|---|---|---|
| 4,124,568 A * | 11/1978 | Zecher et al. ................. 528/59 |
| 4,407,761 A | 10/1983 | Blum et al. |
| 4,705,651 A | 11/1987 | Staibano et al. |
| 4,922,007 A | 5/1990 | Kieczykowski et al. |
| 5,019,651 A | 5/1991 | Kieczykowski et al. |
| 5,908,959 A | 6/1999 | Kubela et al. |
| 6,201,148 B1 * | 3/2001 | Lidor-Hadas et al. ......... 562/13 |
| 6,573,401 B1 | 6/2003 | Bosch i Llado et al. |
| 7,009,071 B2 * | 3/2006 | Dabak et al. ................... 562/13 |
| 7,038,083 B2 * | 5/2006 | Lidor-Hadas et al. ......... 564/15 |
| 2005/0288509 A1 * | 12/2005 | De Ferra et al. ................ 546/22 |
| 2006/0258625 A1 * | 11/2006 | Deshpande et al. ........... 514/80 |
| 2006/0293524 A1 | 12/2006 | Patel et al. |
| 2007/0066569 A1 | 3/2007 | Senthilkumar et al. |
| 2007/0142636 A1 | 6/2007 | Mandava et al. |

FOREIGN PATENT DOCUMENTS

| | | |
|---|---|---|
| WO | WO 95/06052 A1 | 3/1995 |
| WO | WO 98/34940 A1 | 8/1998 |
| WO | WO 02/090367 A1 | 11/2002 |
| WO | WO 03/097655 A1 | 11/2003 |
| WO | WO 2005/044831 A1 | 5/2005 |
| WO | WO 2006/071128 A1 | 7/2006 |

* cited by examiner

*Primary Examiner*—Elvis O Price
(74) *Attorney, Agent, or Firm*—Jay R. Akhave

(57) ABSTRACT

An improved process for bisphosphonylation of acids, substituted acids to obtain compounds with the formula

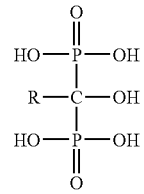

using phosphorus trihalide, phosphorus acid, in presence of phenolic compounds as diluent/solvent.

8 Claims, No Drawings

PROCESS FOR THE PREPARATION OF BIPHOSPHONIC ACIDS

CROSS REFERENCE TO THE RELATED APPLICATION

This application claims the priority of Indian application no: 95/CHE/2006, filed on Jan. 20, 2006.

FIELD OF THE INVENTION

The present invention relates to an improved process for the production of bisphosphonate compounds utilizing new diluents. The process provides for bisphosphonylation of acids, substituted acids to obtain compounds of Formula (I), using phosphorus trihalide, phosphorus acid, in presence of phenolic compounds as diluent/solvent.

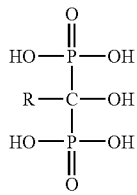

Formula I wherein R represents

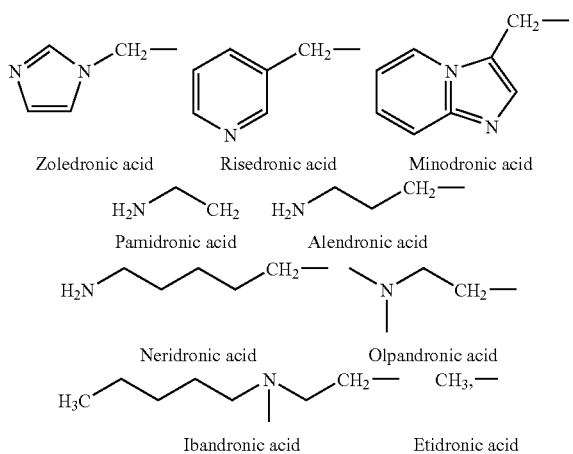

and its salts and hydrates.

BACKGROUND OF THE INVENTION

The bisphosponic acids and their pharmaceutically acceptable salts are an important class of medicaments that act as specific inhibitor of Osteoclast-mediated bone resorption and are useful in the treatment of bone disorders such as Paget's disease and osteoporosis. Bisphosphonates are synthetic analogs of pyrophosphate that bind to the hydroxy-apatite found in the bone.

In particular, bisphosphonates like 3-amino-1-hydroxypropylidene-diphosphonic acid (PAMIDRONIC ACID), 4-amino-1-hydroxybutylidene-1,1-bisphosphonic acid (ALENDRONIC ACID) and 1-hydroxy-2-(3-pyridinyl)ethylidene-1,1-bisphosphonic acid (RISEDRONIC ACID), 1-hydroxy-3-(methylpentylamino)propylidene biphosphonic acid (IBANDRONIC ACID), 1-hydroxyethylidene bisphosphonic acid (ETIDRONIC ACID), 1-hydroxy-2-(1-imidazolyl)ethylidine bisphosphonic acid (ZOLEDRONIC ACID), 2-(imidazo[1,2-a]pyridin-2-yl)ethanoic acid (MINODRONIC ACID) 6-amino-1-hydroxyhexylidene)diphosphonic acid (NERIDRONIC ACID) have been the subject of considerable research efforts in this area.

Several methods have been reported for preparing 1-hydroxy-1,1-bisphosphonic acids. The syntheses are based on reacting a carboxylic acid with a mixture of phosphorous acid and one of the following phosphorous halides: phosphorous trichloride (PCl$_3$), phosphorous oxychloride (POCl$_3$), phosphorous pentachloride (PCl$_5$), phosphorous tribromide (PBr$_3$), phosphorous oxybromide (POBr$_3$) or phosphorous pentabromide (PBr$_5$), then quenching the reaction mixture with water or a nonoxidizing aqueous acid, followed by heating to hydrolyze the phosphorous intermediates to produce the final product.

U.S. Pat. No. 4,407,761 describes the synthesis of 4-amino-1-hydroxybutylidene-1,1-bisphosphonic acid (ALENDRONIC ACID) and other bisphosphonic acids. The reaction can be carried out in the presence of chlorobenzene, which does not solubilize the reaction components and serves only as a heat carrier. The reaction starts as a two-phase system, in which the melted phase gradually thickens into a non-stirrable mass. This semi-solid sticky mass finally turns into a hard, rigid material, coating the walls of the reaction vessel, fouling the reactor and preventing smooth heat transfer and complicating product work-up. Hence, this process is not suitable for commercial production.

Similar process is described in U.S. Pat. No. 5,583,122, to prepare 2-(2-pyridyl)-1-hydroxyethane-1,1-diphosphonic acid and its analogues.

U.S. Pat. No. 4,922,007 describes the use of methanesulfonic acid to overcome the non-homogeneity and solidification problems associated with the formation of intermediates during the bisphosphonation phase.

U.S. Pat. No. 5,019,651 discloses the use of methanesulfonic acid as a carrier/solvent to overcome the above mentioned solubility difficulties.

Although the problems with physical characteristics of the reaction were solved, a safety problem surfaced. Methanesulfonic acid reacts with phosphorus trichloride and under adiabatic conditions the reaction becomes self-heating at 85° C. and an uncontrolled exothermisity occurs at >140° C.

U.S. Pat. No. 5,908,959 describes a process for preparing alendronic acid comprising reacting 4-aminobutyric acid (GABA) with phosphorous acid and phosphorous trichloride in the presence of a polyalkyleneglycol or derivatives thereof. However, it was reported that large quantities of polyalkyleneglycol, as well as toluene and also an additional separation step is needed for the reaction, making it inefficient for use on a large scale. The recovery of polyalkyleneglycol in pure form for reuse is difficult.

U.S. Pat. No. 7,038,083 describes a process for preparing bishphosphonic acid using diluents other than halogenated hydrocarbons. The diluents employed in this process include aromatic hydrocarbons such as toluene, xylene and benzene and inert silicone fluids such as polymethylphenylsiloxane. This process also uses a co-diluent such as orthophosphoric acid. In this process the bisphosphonic acid is isolated from the suspension. Isolating the product from the suspension is tedious industrially and must be avoided.

WO 2006/071128 describes a process for the preparation of Risedronate sodium wherein aqueous solution of 3-pyridinyl acetic acid hydrochloride is added drop wise to phosphorus trichloride at a temperature of 0-5° C. After completion of the reaction excess phosphorus trichloride is removed by high vacuum distillation. Though, this process avoids the use of a suitable diluent, it suffers from the drawback of distilling phosphorus trichloride. The reaction mixture becomes very viscous without a solvent.

WO 98/34940 employs polyalkylene glycols as reaction solvents for synthesizing alendronic acid. However, these solvents have a high cost and are difficult to eliminate from the finished product, given their high boiling point.

WO 02/090367 teaches the use of aralkyl or alkyl ethoxylates or triglycerides such as plant or animal oils for solubilization of the reaction mixture.

US 2006/0258625 A1 describes a process for preparation of a series of bisphosphonic acids as shown below:

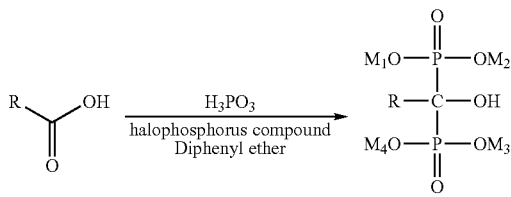

wherein R represents different alkyl derivative part of bisphosphonic acids, $M_1$, $M_2$, $M_3$, $M_4$ represents hydrogen or a monovalent cation. This publication describes the preparation of the bisphosphonic acid derivatives using diphenyl ether as a carrier/solvent. The solvents used in this publication are suitable for laboratory preparation of gram quantities of the product, however for commercial production it is not the preferred choice of solvent.

Therefore, a need to provide a carrier/solvent, for the manufacture of bisphosphonic acids, especially Risedronic acid, Alendronic acid, and Ibandronic acid is needed, which is cheaper, does not cause solidification of the reaction and can be easily recovered and recycled.

We have now found that, in the process of the present invention, if the reaction of carboxylic acid or its salt with phosphorous acid and a halophosphorous compound is carried out in presence of a phenolic compound, the fouling caused by solidification is reduced and results in bisphosphonates of Formula (I) in high yield and high purity.

OBJECTIVE OF INVENTION

The main objective of the present invention is to provide a simple and effective process for the preparation of bisphosphonates of high purity on a commercial scale.

SUMMARY OF THE INVENTION

The present invention relates to an improved process for the preparation of bisphosphonates of compound of Formula (I),

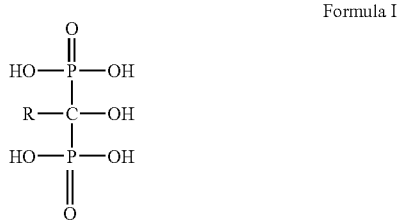

Formula I wherein R represents

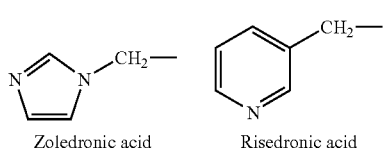

Zoledronic acid  Risedronic acid

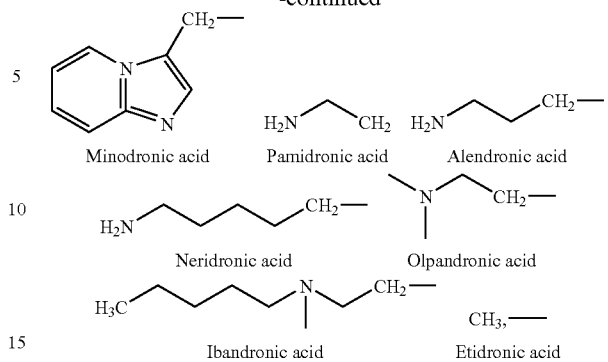

Minodronic acid  Pamidronic acid  Alendronic acid

Neridronic acid  Olpandronic acid

Ibandronic acid  Etidronic acid and its salts and hydrates, which comprises reacting a carboxylic acid compound of Formula (II),

Formula II wherein R is defined above, with either phosphorus acid or in combination with halophosphorus compound in a solvent/diluent consisting of phenol or substituted phenols.

DETAILED DESCRIPTION OF THE INVENTION

The present invention provides the use of commercially available phenol or substituted phenols, which have low cost, easily available and have low toxicity. By conducting the reaction in phenol or substituted phenols, the reaction remains easily stirrable fluid, thus allowing complete conversion of carboxylic acid providing excellent yields and better purity of the bisphosphonates.

The reaction of carboxylic acid or its salt of Formula (II) with either phosphorous acid or in combination with a halophosphorous compound is carried out in a phenolic compound selected from phenol or substituted phenols such as o-cresol, m-cresol, p-cresol, o-fluorophenol, m-fluorophenol, p-fluorophenol, o-chlorophenol, m-chlorophenol, p-chlorophenol, o-bromophenol, m-bromophenol, p-bromophenol, o-iodophenol, m-iodophenol, p-iodophenol, o-aminophenol, m-aminophenol, p-aminophenol, o-nitrophenol, m-nitrophenol, p-nitrophenol, 2,4-dinitrophenol, 2,6-ditertiary butyl-4-methyl phenol etc. The reaction is carried out at a suitable temperature of about 40° C. to 75° C., most preferably 65° C. to 70° C. at which phosphonylation reaction is completed. The halophosphorous compound is selected from phosphourus trichloride, phosphourus pentachloride, phosphourus oxychloride, phosphourus tribromide, phosphourus oxybromide, phosphourus pentabromide or mixtures thereof.

The compound of Formula (II) is selected from a group consisting of 4-aminobutyric acid, 3-aminopropionic acid, 3-pyridyl acetic acid, 1-imidazoylacetic acid, N-(n-pentyl)-N-methyl-3-aminopropionic acid, 2-(imidazo[1,2-a]pyridin-2-yl)ethanoic acid, and 6-aminohexanoic acid, 3-(dimethylamino)propionic acid and the hydrochlorides thereof.

After the completion of reaction, as ascertained by the HPLC/TLC detection methods, water is added to the reaction mixture and stirred for about 4 to 6 hrs. The aqueous layer is separated and the bisphosphonic acid of Formula (I) is precipitated by the addition of lower alcohol selected from methanol, ethanol, isopropanol etc.

The preferred ratio of carboxylic acid of Formula (II) to phosphorus acid and to halophosphorus compound is about 1:1.25:2 to 1:4:4 and phenol can be used in an amount of about 4 to 8 volumes based on weight of the carboxylic acid of Formula (II).

Bisphosphonic acids prepared according to the process of the present invention are converted into their pharmaceutically acceptable salts such as sodium, by methods reported in the prior-art.

Bisphosphonic acids prepared according to the process of the present invention can also be converted into their pharmaceutically acceptable salts directly from the reaction mixture without isolating bisphosphonic acids.

The following examples, to prepare bisphosphonates, will illustrate the nature of the invention and are provided for illustrative purpose only and should not be construed to limit the scope of the invention:

EXAMPLE 1

Preparation of 1-hydroxy-2-(3-pyridinyl)ethylidene-1,1-bisphosphonic acid (Risedronic acid)

A mixture of phosphorus acid (35.9, 0.44 moles), 3-pyridylacetic acid (20 g, 0.15 moles) and phenol (80 g) were heated to 65° C. and phosphorus trichloride (68.2 g, 0.49 moles) was slowly added over a period of 30 min to 1 h while maintaining the temperature at 65-70° C. The reaction was allowed to continue for 4 h, after completion of the $PCl_3$ addition. Then the reaction mixture was hydrolyzed by addition of water (160 ml) at 95° C. for 6 h. Aqueous layer was separated and methanol (320 ml) was added where upon the product precipitated out. The resulting precipitate was cooled to 0° C. and aged for 2 h. The obtained white product was filtered, washed with methanol (2×20 ml) and dried to obtain 26 g of Risedronic acid (Purity: >99%).

EXAMPLE 2

Preparation of 1-hydroxy-2-(3-pyridinyl)ethylidene-1,1-bisphosphonic acid (Risedronic acid)

A mixture of phosphonic acid (89.7 g, 1.09 mole), 3-pyridylacetic acid (50 g, 0.36 moles) and p-Cresol (230 g) were heated to 65° C. and phosphorus trichloride (170.5 g. 1.24 moles) added in 1 h and maintained for 4 h at 65-70° C. The reaction mass was cooled to 10° C. and pre-cooled DM water (800 ml) was added, and then heated to 95° C. The reaction mixture was maintained at 95-100° C. for 6 h. Cooled to 40° C., methanol (800 ml) was added and stirred for 2 h at 2-5° C., filtered and washed with methanol (2×250) and dried to obtain 60 g of Risedronic acid.

EXAMPLE 3

Preparation of 1-hydroxy-2-(3-pyridinyl)ethylidene-1,1-bisphosphonic acid (Risedronic acid)

A mixture of phosphorus acid (134 g, 1.64 moles), 3-pyrdiylacetic acid (75 g, 0.55 moles) and p-nitrophenol (442.5 g) were heated to 65° C. and phosphorus trichloride (259.7 g, 1.89 moles) was slowly added over a period of 2 h at 60-70° C. The reaction mass was allowed to continue for 4 h, after completion of the $PCl_3$ addition. The reaction mixture was hydrolyzed by slow addition of water (750 ml) and conc. HCl (56 ml). After 12 h at 95-100° C., the reaction mass was cooled methanol (1400 ml) was added to precipitate the product. The resulting precipitate was cooled to 5° C. and aged for 2 h. The product was filtered, washed with precooled mixture of methanol and water (1:1 v/v) (2×110 ml) and dried to obtain 137 g of Risedronic acid (purity >98.5%)

EXAMPLE 4

Preparation of 4-amino-1-hydroxybutylidene-1,1-bisphosphonic acid sodium trihydrate (Alendronate sodium)

A mixture of phosphorus acid (596.5 g, 7.27 moles), 4-aminobutyric acid (250 g, 2.42 moles) and phenol (1.0 Kg) were heated to 65° C. and phosphorus trichloride (1.16 Kg, 8.48 moles) was slowly added over a period of 2 h to 2 h 30 minutes at 55-70° C. The reaction was allowed to continue for 4 h. Then the reaction mixture was hydrolyzed by addition of water (2.5 lit) at 100-105° C. for 6 to 8 h. Aqueous layer was separated and washed with toluene (2×0.5 lit). The pH of the aqueous layer was adjusted to 4.3 to 4.5 using 50% sodium hydroxide solution and cooled to 0-5° C. and the reaction mass was stirred for about 4 to 5 h. The product was filtered, washed with cold water, followed by ethanol (0.5 lit) and dried to obtain 375 g of Alendronate sodium trihydrate (HPLC purity >99%).

EXAMPLE 5

Preparation of 4-amino-1-hydroxybutylidene-1,1-bisphosphonic acid sodium trihydrate (Alendronate sodium)

A mixture of phosphorous acid (16 g, 0.1948 moles), 4-aminobutyric acid (10 g, 0.097 moles) and p-cresol (40 g, 0.37 moles) were heated to 50-55° C. and phosphorous trichloride (46.6 g, 0.3394 moles) was slowly added over a period of 1 h. The reaction was allowed to continue at the same temperature for a further period of 2 h. The reaction mass was treated with DM water (40 ml) and raised the temperature to 100-105° C. and maintained for a further period of 6 h. The reaction mass was cooled to 20-25° C. and extracted the excess 4-methyl phenol with toluene (2×20 ml) and the pH of aqueous layer was adjusted to 4.3-4.4 using 50% w/w aqueous sodium hydroxide solution. The reaction mass was cooled to 0-5° C. and stirred for a period of 4 h. The crystalline product was filtered and washed with cold water (50 ml) followed by 95% ethanol (75 ml) and dried to obtain 12.4 g of alendronate sodium trihydrate (HPLC purity >99%).

EXAMPLE 6

Preparation of 4-amino-1-hydroxybutylidene-1,1-bisphosphonic acid sodium trihydrate (Alendronate sodium)

A mixture of 2,6-ditertiary butyl-4-methyl phenol (BHT) (42.74 g, 0.1939 moles) and phosphorous acid (11.93 g, 0.1454 moles) were heated to 75-80° C. to get a clean molten mass. 4-aminobutyric acid (5 g, 0.04849 moles) was added and the reaction mixture was stirred for 15 or 20 minutes. Phosphorous trichloride (24.63 g, 0.1793 moles) was slowly added at ~70° C. in 45-50 minutes and gently refluxed at the same temperature for 1 h. The reaction was continued for 3 h and cooled the reaction mass was cooled to 30-35° C. followed by addition of DM water (40 ml). The resulting solution was heated to 95-100° C. and maintained the same temperature for 9 h. The reaction mass was cooled to 30° C. and extracted with toluene (2×30 ml). The aqueous layer was adjusted to pH 4.3-4.4 with 50% w/w aqueous sodium hydroxide solution. The reaction mass was cooled to 0-5° C. and maintained for 4 h to complete the crystallization. The product was filtered, washed with cold DM Water (20 ml), followed by 95% ethanol (20 ml) and dried to obtain 11 g of alendronate sodium trihydrate (HPLC purity >99%).

EXAMPLE 7

Preparation of
4-amino-1-hydroxybutylidene-1,1-bisphosphonic
acid sodium salt (Alendronate sodium)

A mixture of phosphorous acid (11.93 g, 0.1455 moles) and 4-nitrophenol (26.93 g, 0.1941 moles) was heated to 85-87° C. to get a melt to which 4-aminobutyric acid (5 g, 0.0485 moles) was added. The temperature of the reaction mass was brought down to 60-65° C., and phosphorous trichloride (22.64 g, 0.1649 moles) was added at the same temperature in 45 minutes and maintained for 4 h. The reaction mass was cooled to 25-30° C. and DM water (40 ml) was added carefully during 20 minutes. The temperature of the resulting mixture was raised to 95-100° C. and maintained the same temperature for 6 h to complete hydrolysis. Temperature of the reaction mass was adjusted to 50-55° C. and methanol (200 ml) was added and stirred for 1 h. The reaction mass was cooled to 10-15° C. and stirred for 2 h to complete the crystallization. Filtered the product, washed with methanol (2×20 ml) and dried under reduced pressure at 45-50° C. to get 4 g of alendronic acid (HPLC purity >98%).

The alendronic acid thus obtained could be converted to the monosodium salt or its trihydrate by methods known in the art.

What is claimed is:

1. An improved process for the preparation of bisphosphonic derivatives of Formula (I),

Formula I wherein R represents

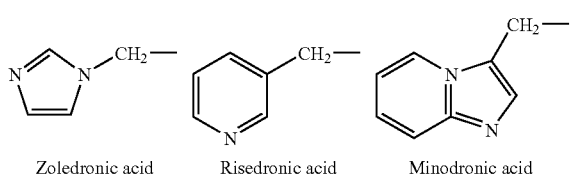

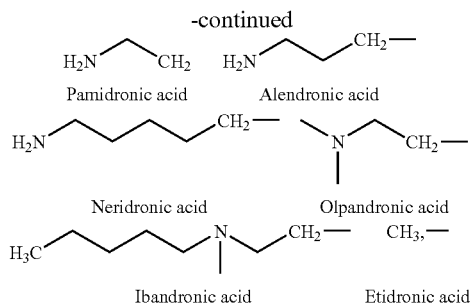

and its salts and hydrates, which comprises reacting a carboxylic acid compound of Formula (II),

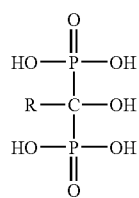

Formula II with either phosphorus acid or phosphorus acid in combination with halophosphorus compound, in a solvent consisting of phenol or substituted phenols, wherein the reaction mass is maintained as a uniform single phase.

2. The process according to claim 1, wherein the halophosphorus compound is selected from phosphorus trichloride, phosphorus pentachloride, phosphorus oxychloride, phosphorus tribromide, phosphorus oxybromide, phosphorus pentabromide or mixtures thereof.

3. The process according to claim 1, wherein the solvent is selected from phenol or substituted phenols.

4. The process according to claim 3, wherein phenol or substituted phenols is selected from o-cresol, m-cresol, p-cresol, o-fluorophenol, m-fluorophenol, p-fluorophenol, o-chlorophenol, m-chlorophenol, p-chlorophenol, o-bromophenol, m-bromophenol, p-bromophenol, o-iodophenol, m-iodophenol, p-iodophenol, o-aminophenol, m-aminophenol, p-aminophenol, o-nitrophenol, m-nitrophenol, p-nitrophenol, 2,4-dintrophenol, 2,4,6-trinitrophenol 2,6-ditertiary butyl-4-methyl phenol or mixtures thereof, more preferably phenol.

5. The process according to claim 1, wherein the carboxylic acid is selected from the group consisting of 4-aminobutyric acid, 3-aminopropionic acid, 3-pyridyl acetic acid, 1-imidazoylacetic acid, N-(n-pentyl)-N-methyl-3-aminopropionic acid, 2-(imidazo[1,2-a]pyridin-2-yl)ethanoic acid, and 6-aminohexanoic acid, 3-(dimethylamino)propionic acid.

6. The process according to claim 1, wherein the carboxylic acid is 4-aminobutyric acid.

7. The process according to claim 1, wherein the carboxylic acid is 3-pyridylacetic acid.

8. The process according to claim 1, wherein the carboxylic acid is N-(n-pentyl)-N-methyl-3-aminopropionic acid.

* * * * *

Adverse Decisions in Interference

Patent No. 7,528,280, Subba Reddy Danda, Narayan K.A.S.S. Garimella, Srinivasa Rao V.N. Divvela, Ramesh Dandala and Sivakumaran Meenakshisunderam, PROCESS FOR THE PREPARATION OF BIPHOSPHONIC ACIDS, Interference No. 105,713, final judgment adverse to the patentees rendered December 1, 2009, as to claims 1-8.

*(Official Gazette, July 27, 2010)*